United States Patent [19]

Seemuth

[11] Patent Number: 4,554,387
[45] Date of Patent: Nov. 19, 1985

[54] RING OPENING OF CYCLIC NITRO KETONES

[75] Inventor: Paul D. Seemuth, Baton Rouge, La.

[73] Assignee: Ethyl Corporation, Richmond, Va.

[21] Appl. No.: 604,891

[22] Filed: Apr. 27, 1984

[51] Int. Cl.$^4$ .............................................. C07C 79/18
[52] U.S. Cl. .................................................... 568/704
[58] Field of Search ........................................ 568/704

[56] References Cited

U.S. PATENT DOCUMENTS

| | | | |
|---|---|---|---|
| 3,024,288 | 3/1962 | Klager | 568/704 |
| 3,297,769 | 1/1967 | Michalski et al. | 568/704 |
| 3,544,062 | 2/1971 | Tindall | 568/704 |
| 3,796,734 | 3/1974 | Duranleau et al. | 568/704 |
| 3,968,147 | 7/1976 | Solodar | 568/704 |

OTHER PUBLICATIONS

Severin et al., "Chem. Ber", vol. 98 (4), pp. 1159–1163 (1963).
Dampawan et al., "Tetrahedron Letters", pp. 135–138 (1982).
Schechter et al., "J. Amer. Chem. Soc.", vol. 74 (14), pp. 3664–3668 (1952).

Primary Examiner—Werren B. Lone
Attorney, Agent, or Firm—Donald L. Johnson; John F. Sieberth; John F. Hunt

[57] ABSTRACT

Macrocyclic ring opening reaction. The 2-nitro cycloalkan-1-ones and similar 2-nitro heterocyclic compounds are ring opened by reduction of the carbonyl oxygen with an anionic species such as $NaBH_4$. An $\alpha,\omega$-nitro alcohol is recovered.

28 Claims, No Drawings

RING OPENING OF CYCLIC NITRO KETONES

BACKGROUND OF THE INVENTION

1. Field of the Invention

The present invention relates generally to cyclic compounds and in particular to the reduction of cyclic nitro ketones to open the ring of the cyclic compound and form a nitro alcohol product.

2. Description of the Prior Art

In the past the art has shown that cyclic compounds may be reacted with other reagents to form cyclic products or products in which the ring has been opened. However, there exists a need in the prior art for various ring opened compounds of fairly large molecular weight and there exists a need to be able to produce such compounds from cyclic precursors.

SUMMARY OF THE INVENTION

The present invention is directed to the novel ring opening of cyclic nitro ketones to form corresponding acyclic $\alpha,\omega$-nitro alcohols. By the present invention, macrocyclic nitro ketones are treated with reducing agents to cleave the ring, convert the oxygen of the carbonyl group (ketone function) to a carbinol (C-OH) and form a compound having on one end of the structure a nitro group and at the other end of the structure a hydroxy group thus forming a nitro alcohol. That is, according to the invention, the $C_1-C_2$ bond of the large cyclic compound is cleaved while the carbonyl group of the $C_1$ carbon atom is converted to the carbinol (alcohol) function.

The process of the invention provides $\alpha,\omega$-nitro alcohols having between the nitro and OH functions at least five carbon or other atoms which form the cyclic precursor. The products of the invention may be used to further produce various other usable compounds such as amino alcohols by reduction of the nitro group to an amine function. The amino alcohols may be used as a chain extender or cross linker for polyurethanes, epoxides, and the like. Nitro acids and esters may be formed from the nitro alcohols for synthetic intermediates. Also, amino aldehydes may be formed for antibiotic synthesis. Long chain acyclic compounds with substitution at opposite ends of the carbon chain are relatively difficult to make by other procedures and the present invention provides a family of such compounds by an easy route from a macrocyclic nitro ketone.

The present invention is a process for ring opening a cyclic compound having a ring structure of at least seven members including a carbonyl group between a carbon atom and a nitro-substituted carbon atom, said process comprising contacting said cyclic compound with a reducing agent whereby said carbonyl group is reduced to a carbinol group, and opening said ring structure between the carbonyl group and the nitro-substituted carbon atom.

The present invention is also a process for ring opening a cyclic compound of at least seven members including in the ring a ketonic $\alpha$ carbon atom adjacent a nitro-substituted $\omega$ carbon atom and also adjacent a $\beta$ carbon atom, said process comprising reacting, in an innocuous liquid reaction medium, said cyclic compound with a quantity of metal hydride to provide sufficient hydride ions to reduce the carbonyl group to a carbinol group and cleave the ring between the carbonyl group and said nitro-substituted carbon atom.

The present invention is also a process for ring opening a $C_7-C_{30}$ 2-nitro cycloalkan-1-one, said process comprising (i) reacting said 2-nitro cycloalkan-1-one with an alkali metal or alkaline earth metal boron tetrahydride, in an innocuous liquid reaction medium to reduce the ketone group to a hydroxyl group and cleave the ring between the ketone group and the 2-nitro group; and (ii) providing a proton source to form a nitro alcohol.

DESCRIPTION OF THE PREFERRED EMBODIMENTS

According to the present invention treatment of a cyclic nitro ketone results in reduction of the carbonyl group to the alcohol function but, at the same time the $C_1-C_2$ bond is ruptured resulting in an acyclic product having at one end thereof a nitro function and at the other end a hydroxy function. The reaction provides a route to producing long chain compounds containing different functionalities at the terminal ends of the hydrocarbon or heteroatomic backbone. Such functionalities can then be transformed, independently of one another, to other reactive species. The route of the present invention allows synthesis of long chain $\alpha,\omega$-amino alcohols for use as polyurethane chain extenders as well as a host of other related $\alpha,\omega$ compounds.

According to the present invention a cyclic compound of at least seven members having in its ring structure a carbonyl group disposed between a carbon atom and a nitro-substituted carbon atom, is treated so as to reduce the carbonyl group to a carbinol group and open the ring structure between the carbonyl group and the nitro-substituted carbon atom thereby forming a nitro alcohol. That is, the ketonic function is reduced to form a product having at the $\alpha$-position a hydroxy group and at the $\omega$-position the nitro function intact from the cyclic precursor. Thus, the $C_1$ or first carbon atom of the cyclic compound which is reacted with a reducing agent has a bond to a first carbon atom adjacent thereto on the ring, which carbon atom may be unsubstituted or substituted with one or two hydrocarbon groups, preferably alkyl or aryl, more preferably lower alkyl. The $C_1$ or first carbon atom of the ring also has a double bond oxygen or ketone function thus supplying a carbonyl function as a portion of the ring. Finally, the $C_1$ or first carbon atom of the ring has a fourth bond to the $C_2$ or second carbon atom of the ring. The second carbon atom of the ring has bonded thereto a nitro ($NO_2$) function.

Alternatively, the carbon atom of the carbonyl function in the ring may be referred to as the $\alpha$ carbon atom and the adjacent carbon atom having a nitro substituent may be referred to as the $\omega$ carbon atom. Treatment of the precursor cyclic compounds of the invention so as to convert the oxygen of the carbonyl function to a hydroxy group also results in cleavage or opening of the ring between the $\alpha$ and $\omega$ ($C_1$ and $C_2$) carbon atoms of the ring. This forms a noncyclic compound having at one end thereof a nitro function and at the other end thereof a hydroxy group to form the alcohol. While the compound is referred to as noncyclic, there may be other substituents from the precursor cyclic compound which remain as cyclic moieties of the nitro alcohol product, but the cyclic nitro ketone is reduced to form the backbone of the nitro alcohol.

A preferred class of large cyclic compounds of the invention are those of structure I:

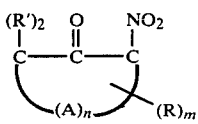

wherein n is at least 4; the A are independently selected from the group consisting of O, S, P, N, B, Si, or C, only one A being other than C; the R' are independently selected H or hydrocarbons; the R are substituents independently selected from alkyl, aryl, alkaryl, aralkyl, halogen, nitro, another ring structure, and amine; and m is zero to n.

The cyclic or macrocyclic compounds may be hydrocarbon or heterocyclic ring structures with or without substituents. However, the atom adjacent to the carbonyl function must be a carbon atom. Thus for example, the atom adjacent the carbonyl function may be not be an oxygen which is a member of the ring since this would form an ester function. However, other members of the ring structure may be oxygen, sulphur, or other compounds without detracting from the process of the invention. Furthermore, fused ring structures may be used. Thus, the following structure A is not suitable for the invention.

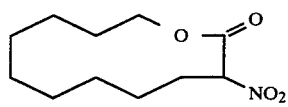

However, the following structures B and C are suitable for the invention:

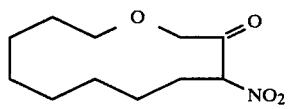

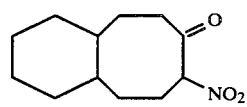

Heterocyclic compounds suitable for the invention include those disclosed by T. Severin et al. in Addition of Ketones to Nitro Arenes (II), Chem. Ber. 98 (4), 1159–63 (1965) which is incorporated herein by reference in its entirety.

Unsaturated heterocyclic compounds known per se may be reduced by conventional means to provide heterocyclic starting materials of the invention. Treatment of the unsaturated compounds with $H_2$ over a catalyst will selectively hydrogenate the unsaturated large rings under moderate conditions. Such starting materials fall within the group of compounds in structure I. Also, cyclic compounds may be nitrated with $HNO_3$ or other reagent to provide a starting material of the invention.

A more preferred class of cyclic compounds of the invention are the 2-nitro cycloalkan-1-ones having at least seven members in the cyclic structure with a carbonyl function disposed between a carbon atom and the nitro-substituted carbon atom. Examples of these more preferred compounds of the invention are:
2-nitro cyclooctan-1-one;
2-nitro cyclononan-1-one;
2-nitro cycloundecan-1-one;
2-nitro cyclododecan-1-one;
2-nitro cyclopentadecan-1-one;
2-nitro-12-methylcyclododecan-1-one;
2-nitro-12-propylcyclododecan-1-one;
2-nitro cyclodocosan-1-one; and
2-nitro eicosan-1-one.

The preferred compounds of the invention generally have 7–30 ring members, preferably carbon atoms with various substituents. The substituents may be the alkyl groups: methyl, ethyl, propyl, n-butyl, isobutyl, tert-butyl, pentyl, hexyl, etc.; aryl groups: benzyl,, phenyl, α-methylbenzyl, etc.; esters; acids; cycloalkyls: cyclopentyl, cyclohexyl, etc.; other nitro groups, halogens: fluorine, chlorine, bromine, iodine; and the cyano function (CN). In general, the substituents on the ring may be any groups that tolerate the reaction conditions and the ring members may have more than one group substituted thereon. As mentioned above, fused ring systems are suitable for the invention and one or more hetero atoms such as oxygen or nitrogen may be included as a member of the ring except where the hetero atom is adjacent to the carbonyl function.

The reaction of the present invention may be carried out at any temperature within a broad range including ambient temperatures. A preferred range is about 0°–40° C. and a more preferred range is 10°–25° C. The reaction is preferably carried out within this temperature range so as to control the rate of the reaction and accomplish the reduction of the oxygen atom of the carbon oxygen double bond.

The reaction time may vary depending upon the reducing agent used or the particular precursor cyclic compound but 30 minutes with stirring is typically an adequate reaction time for 2-nitro cycloalkan-1-ones. Any reaction time sufficient for the reaction to be completed is suitable so as to provide a good yield. The completion of the reaction may be determined by monitoring with thin layer chromatography (TLC).

Preferably, a solvent is used to carry out the invention. Any solvent is suitable so long as it does not interfere with the reaction and so long as the precursor cyclic compound is contacted with the anionic agent or other reducing agent to prepare a noncyclic nitro alcohol from the precursor cyclic compound. Suitable solvents include ethanol, isopropanol, toluene, diethylether, tetrahydrofuran, dimethoxyethane, and other glycols. Most typical organic solvents are compatible with the various reducing species and are suitable for the invention if they do not react with the reducing species. The preferred solvents are ethanol and tetrahydrofuran. Methylene chloride and carbon tetrachloride may also be used.

In a preferred embodiment of the invention, a cyclic precursor is reacted in a batch process with a reducing agent providing hydride ions to the cyclic ketone. Of course, a continuous reaction process is also available with the invention. Various anionic reactants which provide a hydride species are suitable for reducing the carbon of the carbon oxygen double bond in the cyclic compound precursor.

According to the invention, the preferred reactants for cleaving the cyclic compound to form a nitro alcohol are the metal hydrides and mixed metal hydrides. More preferred are the metal tetrahydrides and mixed metal tetrahydrides. Suitable metal hydrides and mixed metal hydrides of the invention are $NaBH_4$, $NaBH_3CN$, $LiBH_4$, $KBH_4$, $CsBH_4$, $RbBH_4$ (the alkali metal boron tetrahydrides). Also suitable are the alkaline earth boron hydrides such as $Mg(BH_4)_2$, $Ca(BH_4)_2$ and the like. Various aluminum hydrides are also suitable for the invention such as $LiAlH_4$, $AlH_3$, $LiAl(OR)_n H_{4-n}$ where n=1 to 3 and R=alkyl, $NaAlEt_2H_2$, $(isobutyl)_2 AlH$ and the like. The most preferred reducing agent or anionic reactant providing hydride species according to the invention is $NaBH_4$.

Reactants such as $NaBD_4$ or $LiAlD_4$ are also usable with the invention and are equivalent hydride-like reducing species.

Where "hydride" is used herein, deuteride could be substituted.

The complex of $BH_3$ with tetrahydrofuran (THF) is not an anionic agent and is not suitable to cleave or open the ring of the cyclic compounds of the invention.

According to the invention, it is preferable to add the nitro ketone cyclic compound to a liquid reaction medium containing hydride species such as a solution of sodium borohydride in ethanol. The reaction is readily monitored by thin layer chromatography.

A nitro alcohol is recovered from the reaction mixture after ring-opening. The nitro alcohol may be recovered by providing a proton source or donor. Preferably the protons are provided by a dilute acid such as HCl, $H_2SO_4$, $HNO_3$, and other mineral acids.

The following nonlimiting examples serve to illustrate the process of the invention.

EXAMPLE 1

Approximately 2.89 grams (0.0764 moles) of $NaBH_4$ were added to 60 milliliters of 100% ethanol in a 500 milliliter flask. To the suspension was added portion-wise about 12.5 grams of 2-nitro cyclododecan-1-one while maintaining the temperature at about 15° C. in an ice bath. The solution slowly turned milky and cloudy as a gel formed. The reaction slowly warmed to room temperature though for a brief period the temperature did reach about 28° C. when the ice bath was taken away after the addition was completed. Thin layer chromatography analysis showed a trace of the ketone still present. An additional 0.78 grams (0.0206 moles) of $NaBH_4$ was added and the suspension allowed to stir overnight with a magnetic stirrer. A gel-like precipitate formed. The precipitate disappeared and a brownish gummy mass formed as the pH was lowered. The final reaction mixture, at pH2, was clear with a gummy mass present (after addition of approximately 75 milliliters of 2% HCl). The water and ethanol were stripped under vacuum to leave a tan colored solid. The tan colored mass was dissolved in ethanol as best possible, filtered, and kept separate. Further analysis showed that the main product no longer contained a carbonyl function but rather an OH function. A very small but detectable portion of a compound having a carbon oxygen double bond was still present. The nitro function was clearly still present by infrared analysis. Approximately 12.6 grams of product was obtained.

NOTE: The amount of the nitro ketone used was 0.055 moles and the amount of the $NaBH_4$ used was 0.097 moles.

EXAMPLE 2

Approximately 4.5 grams (0.1189 mole or 2.1 equivalents) hydride were added to 80 milliliters of ethanol. While the suspension was maintained at 15°–16° C., about 12.84 grams (0.0565 moles) of solid 2-nitro cyclododecan-1-one were added in portions. Some foaming was seen although this presented no problem. The addition of the nitro ketone took about 20 minutes. The reaction was allowed to stir for about 2½ days. Thin layer chromatography was performed using a methylene chloride solvent. No ketone remained in the product sample. To the product reaction mass was added enough 2% HCl to dissolve the solid present and turn the solution to a yellowish color. At a pH of 2 the reaction mass was clear. This required about 175 milliliters of 2% HCl. The water/ethanol product was transferred to a round bottom flask and solvent was removed. The product was extracted using methylene chloride (two 150 milliliter portions) and the combined organics were dried over magnesium sulfate. The magnesium sulfate was filtered off under vacuum to remove solvent and the yellow liquid which crystallized rapidly was recovered. By gas chromatography, thin layer chromatography, nuclear magnetic resonance spectroscopy, and infrared analysis, the 12.95 grams of product was determined to be 12nitro dodecan-1-ol.

EXAMPLE 3

For purposes of analytical determinations, the process of Example 2 was carried out with sodium boroduteride ($NaBD_4$) To 40 milliliters of absolute ethanol was added about 2.5 grams of $NaBD_4$ (0.05972 mole). The suspension was stirred and about 6.78 grams (0.02986 mole) solid 2-nitro cyclododecan-1-one were added in portions maintaining the temperature at about 15° C. The addition took about 20 minutes and some foaming was evidenced (gas evolution). After the addition was complete, a white, fairly thick precipitate was evident. An additional 10 milliliters of ethanol was added to facilitate stirring. The reaction mass was allowed to warm to room temperature and stirred overnight. The acidification process of the previous examples was followed and the precipitate again disappeared at a pH of 2 after addition of about 100 milliliters of 2% HCl. The solution had a fine white appearance. The ethanol/water was stripped to about ½ the starting volume and the water-oil emulsion left was taken up in methylene chloride. After two washings with methylene chloride, the combined organic layers were dried over magnesium sulfate and the solvent stripped off and vacuumed. A yellow oil was recovered which solidified fairly rapidly. The material melts at 40° C. and approximately 6.95 grams of product were recovered. Using the deuterium ions supplied in place of hydride ions from the $NaBD_4$, the nuclear magnetic resonance spectroscopy confirmed the ring opening of the cyclic compound to form a dodecanol having a nitro substituent at the opposite end of the hydroxy function. Furthermore, the analysis confirmed that the carbonyl function had been converted to the hydroxy function.

EXAMPLE 3A

The process of Example 3 was repeated using sodium borohydride ($NaBH_4$). To a fresh solution of 2.68 grams (0.07084 moles) of $NaBH_4$ in 40 milliliters absolute ethanol was slowly added about 8.05 grams (0.03542 moles) 2-nitro cyclododecan-1-one while maintaining the temperature of the reaction mixture at 15° C. A white precipitate started to form during addition and gas evolution was evidenced. After 20 minutes, the white precipitate in ethanol was stirred while the temperature rose to ambient and stirring was continued overnight. Nuclear magnetic resonance (NMR) confirmed the identity of the α,ω-nitro alcohol formed and 7.61 grams of product were recovered.

EXAMPLE 3B

The process of Example 3 was repeated using about 1.76 grams (0.0078038 moles) of cyclododecane-1-one with 0.98 grams (0.02341 moles) of NaBD$_4$ in 40 milliliters ethanol at 15° C. The results of the previous experiments were confirmed. An intermediate analysis of the example by thin layer chromatography revealed that some of the ketone was left in the reaction mixture. An additional 0.20 grams (0.0048 moles) NaBD$_4$ was added as excess to react with the nitro ketone. One and one-half hours after the last addition, the thin layer chromatography showed no evidence of ketone remaining in the mixture. The reaction was allowed to stir overnight and approximately 1.64 grams of the product α-nitro-ω-dodecanol were recovered, equivalent to about 91% yield.

EXAMPLE 4

This example demonstrates that macrocyclic nitro ketones, unlike smaller six-membered rings, are not reduced to a cyclic nitro alcohol but rather are preferentially ring opened even without a stoichiometric excess of reducing agent. Although a portion of the nitro ketone starting material remains unreacted, none of the cyclic nitro alcohol is detected.

NaBH$_4$, 0.1664 grams (4.4 millimoles) was added to 40 mls. absolute ethanol in a 100 ml. flask and cooled to 15° C. To this was added portionwise 1.0 gram (4.4 millimoles) 2-nitro cyclododecan-1-one. The reaction mass was allowed to warm to room temperature and a miniscule sample was removed for TLC analysis which showed the presence of an alcohol and a ketone. The reaction mixture was allowed to sit about 2½ days. Further TLC indicated no additional reaction had occurred.

About 10 ml. water were added and then the pH of the reaction mixture was lowered to a value of 2 using 2% HCl (about 7 ml.).

The product was recovered and analyzed in the same manner as Example 1. The conversion of the starting nitro ketone was 70% and the structure of the α,ω-nitro alcohol was confirmed by NMR, IR, GC/MS and TLC.

EXAMPLE 5

In this experiment, a mixture of NaBH$_4$ and NaBD$_4$ was used to study the mechanism of the ring opening reaction. The amounts of materials were very carefully weighed to assure that a 10% excess of the NaBH$_4$/NaBD$_4$ was provided. To a 250 milliliter three necked flask which had been flushed with nitrogen was added 0.2746 grams (7.26 millimoles) NaBH$_4$ and 0.3039 grams (7.26 millimoles) NaBD$_4$. Then 3 grams (13.2 millimoles of 2-nitro cyclododecan-1-one dissolved in 150 milliliters ethanol were added to the flask at 9° C. The addition was at a rate such as to maintain the temperature at about 10°–12° C. and the addition was complete in about 10 minutes. After the addition of the nitro ketone, the flask and contents were allowed to warm to room temperature and stirred overnight. The reaction product was acidified with HCl. Thereafter, the water and ethanol were removed until only 1 or 2 milliliters of liquid remained. Water was added and an oil appeared which was extracted with two 75 milliliter portions of methylene chloride. The sample was dried overnight.

The sample was filtered and solvent stripped and vacuumed so as to recover 3.02 grams of oil that solidified within 1–2 hours. NMR analysis showed some ketone starting material remained in the mass. The total analysis disclosed the ring opened process as expected and shown by the previous examples.

COMPARATIVE EXAMPLE 6

The present example demonstrates that the carbon oxygen double bond of the macrocyclic starting compound must be reduced. That is, the compound must be reacted with an anionic agent which provides hydride ions to form the resulting nitro alcohol product. To a 25 milliliter three neck flask with dropping funnel and nitrogen inlet and thermal well was added 1.5 milliliters of 1 molar (1.32×10$^{-3}$ moles) BH$_3$.THF complex after a nitrogen atmosphere had been established in the flask. About 0.15 grams (0.6599×10$^{-3}$ moles) of 2-nitro cyclododecan-1-one was dissolved in 3.5 milliliters of THF and added to the dropping funnel. The BH$_3$.THF complex was cooled to about 10° C. using ice and the addition to the flask of the nitro ketone solution was started. The temperature rose to about 11.8° C. and held there. After the addition was complete in about 3 minutes, the clear solution was stirred for 1 hour. Thereafter, an additional 1 milliliter of the 1 molar solution of BH$_3$.THF was added to the reaction mixture and the contents of the flask were stirred at room temperature overnight. The resulting clear solution was quenched with 3% NaOH in water. Thereafter the cloudy solution was reduced to a pH of 2 with 2% HCl and methylene chloride was added. The aqueous layer was extracted twice with methylene chloride and the organic portion was combined and dried with magnesium sulfate overnight. The magnesium sulfate was removed by filtration and stripping under vacuum produced a clear oil. The thin layer chromatography analysis was confirmed by infrared spectroscopy and NMR to show that the product was the cyclic 2-nitro cyclododecan-1-ol. Thus the ring had not been cleaved when a nonanionic agent was reacted with the nitro ketone.

EXAMPLE 7

An experiment was carried out to study the solvent effect on the hydride ions for reduction of the carbonyl bond and ring opening of the macrocyclic compound. To a 100 milliliter 3 neck flask flushed with nitrogen was added 0.0275 grams (0.73 millimoles) NaBH$_4$. To this was added 3 milliliters THF which had been dried over 4 A° sieves. In 3 milliliters THF, 0.15 grams (0.66 millimoles) of 2-nitro cyclododecan-1-one was added to the hydride suspension in THF and allowed to stir at room temperature. After about 1 hour the reaction mass started to turn pale milky white and after 2½ hours the medium was milky. The reaction was allowed to stir overnight and produced a milky white product. About 7.5 milliliters of water were added and the solution cleared up to a light yellow. The reaction mass was acidified to a pH of 2 with a few drops of concentrated HCl. The product was extracted with two 25 milliliter portions of methylene chloride and dried over magnesium sulfate. Thereafter the reaction mass was filtered and the solvent removed with vacuum. About 0.14 grams of yellow oil were recovered. Nuclear magnetic resonance spectroscopy confirmed the ring opening in that the starting nitro ketone was no longer present. Further, the product was confirmed to be an α,ω-nitro alcohol (1-nitro dodecan-1-ol).

COMPARATIVE EXAMPLE 8

A hydride reducing agent was reacted with a non-macrocyclic nitro ketone for comparison with the invention. 0.396 Grams (10.5 millimoles) NaBH$_4$ in 30 milliliters ethanol was added to a reaction flask at 15° C., using an ice bath to maintain temperature. About 0.5 grams (0.00349 moles) 2-nitro cyclohexan-1-one were added to the reaction flask and stirred but no solid appeared. Thin layer chromatography revealed the presence of the starting nitro ketone. The mixture was allowed to stir for about 3½ days. Thereafter, water was added and the reaction mass was acidified with about 15 milliliters of 2% HCl to reduce the pH to 2. This mixture was allowed to stir overnight. The solvent was removed in vacuum and the product was extracted with trichloromethane then the recovered organics were dried over magnesium sulfate. The magnesium sulfate was filtered off, and the trichloromethane was removed under vacuum. About 0.45 grams of a brown oil were recovered and hydrogen NMR and gas chromatography with purification confirmed the presence of non-ring opened cyclic nitro alcohol but no desired ring opened reaction products.

EXAMPLE 9

The process of the invention was carried out using an 8 membered ring. About 0.0784 grams (0.0021 moles) of NaBH$_4$ were charged to a 3 neck flask with 4 milliliters absolute ethanol. Thereafter, 0.1774 grams (0.001036 mole) of 2-nitro cyclooctan-1-one in 25 milliliters ethanol was added to the flask at room temperature and an ice bath was applied for cooling. After the addition was complete the reaction mixture was stirred for 4 hours and water and about 4 milliliters of 2% HCl were added to reduce the pH to 2. The water and ethanol were stripped off and a water and oil product remained. An NaCl water solution was used to work up the product. The product was extracted with two 10 milliliter portions of methylene chloride and the combined organics were dried over magnesium sulfate. The solvent was filtered and stripped off so as to recover about 0.10 grams product (55% yield). NMR, GC/mass spec., and IR spectroscopy confirmed the presence of the product as well as about 41.5% of the 2-nitro-1-cyclooctene, a dehydrated non ring opened by-product. The major product was confirmed to be the α,ω-nitro alcohol(1-nitro octan-1-ol).

Various aspects and embodiments of the invention may be varied without departing from the scope or spirit of the invention as defined by the appended claims.

I claim:

1. A process for ring opening a cyclic compound having a ring structure of 7-30 ring members including a carbonyl group between a carbon atom and a nitro-substituted carbon atom, said process comprising contacting said cyclic compound with an anionic reactant that provides a hydride species whereby said carbonyl group is reduced to a carbinol group, and opening said ring structure between the carbonyl group and the nitro-substituted carbon atom.

2. The process of claim 1 wherein said anionic reactant is a metal hydride.

3. The process of claim 2 wherein said metal hydride is a metal tetrahydride.

4. The process of claim 2 wherein said metal hydride is a mixed metal hydride.

5. The process of claim 4 wherein said mixed metal hydride is NaBH$_3$CN.

6. The process of claim 4 wherein said mixed metal hydride is a mixed metal tetrahydride.

7. The process of claim 6 wherein said mixed metal tetrahydride is an alkali metal boron tetrahydride.

8. The process of claim 7 wherein said alkali metal boron tetrahydride is NaBH$_4$.

9. The process of claim 4 wherein said mixed metal hydride is an alkaline earth boron hydride.

10. The process of claim 9 wherein said alkaline earth boron hydride is Mg(BH$_4$)$_2$.

11. The process of claim 1 wherein said cyclic compound is heterocyclic.

12. The heterocyclic compound of claim 11 having a ring member selected from O, S, P, N, B, and Si.

13. The process of claim 1 wherein said compound is substituted on at least one member of the ring structure.

14. The process of claim 1 wherein said cyclic compound is of structure I:

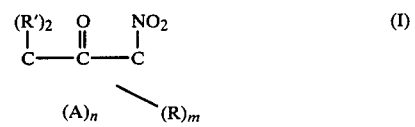

wherein n is at least 4; the A are independently selected from the group consisting of O, S, P, N, B, Si, or C, only one A being other than C; the R' are independently selected H or hydrocarbons; the R are substituents independently selected from alkyl, aryl, alkaryl, aralkyl, halogen, nitro, another ring structure, and amine; and m is zero to n.

15. The process of claim 1 wherein said cyclic compound is a C$_7$-C$_{30}$ 2-nitro cycloalkan-1-one.

16. The process of claim 15 wherein said C$_7$-C$_{30}$ 2-nitro cycloalkan-1-one is 2-nitro cyclooctan-1-one.

17. The process of claim 15 wherein said C$_7$-C$_{30}$ 2-nitro cycloalkan-1-one is 2-nitro cyclododenan-1-one.

18. The process of claim 1 wherein said anionic reactant is present in an amount sufficient to provide at least four hydride ions per mole part of said cyclic compound.

19. The process of claim 3 wherein 0.25 to 3.0 mole parts of said metal tetrahydride are present per mole part of said cyclic compound.

20. The process of claim 1 further comprising recovering a nitro alcohol.

21. A process for ring opening a cyclic compound of 7-30 ring members including in the ring a ketonic α carbon atom adjacent a nitro-substituted ω carbon atom; and also adjacent a β carbon atom, said process comprising reacting, in an innocuous liquid reaction medium, said cyclic compound with a quantity of metal hydride to provide sufficient hydride ions to reduce said carbonyl group to a carbinol group and cleave the ring between said carbonyl group and said nitro-substituted carbon atom.

22. The process of claim 21 further comprising recovering a nitro alcohol.

23. The process of claim 22 wherein said nitro alcohol is recovered by providing a proton source to the ring-opened compounds.

24. The process of claim 21 further comprising adding an acid to form an α,ω-nitro alcohol.

25. The process of claim 21 wherein said metal hydride is a tetrahydride and the quantity of said tetrahydride is about 0.25 to 3.0 moles per mole of said cyclic compound.

26. A process for ring opening a $C_7$–$C_{30}$ 2-nitro cycloalkan-1-one, said process comprising (i) reacting said 2-nitro cycloalkan-1-one with an alkali metal or alkaline earth metal boron tetrahydride, in an innocuous liquid reaction medium to reduce the ketone group to a hydroxyl group and cleave the ring between the ketone group and the 2-nitro group; and (ii) providing a proton source to from a nitro alcohol.

27. The process of claim 26 wherein said 2-nitro cycloalkan-1-one is 2-nitro cyclooctan-1-one.

28. The process of claim 26 wherein said 2-nitro cycloalkan-1-one is 2-nitro cyclododecan-1-one.

* * * * *

UNITED STATES PATENT AND TRADEMARK OFFICE
CERTIFICATE OF CORRECTION

PATENT NO. : 4,554,387

DATED : NOVEMBER 19, 1985

INVENTOR(S) : PAUL D. SEEMUTH

It is certified that error appears in the above-identified patent and that said Letters Patent is hereby corrected as shown below:

Column 4, line 12, reads "benzyl,," and should read -- benzyl, --.

Column 6, line 21, reads "12 nitro" and should read -- 12-nitro --.

Column 10, lines 21-26, Structure (I), reads

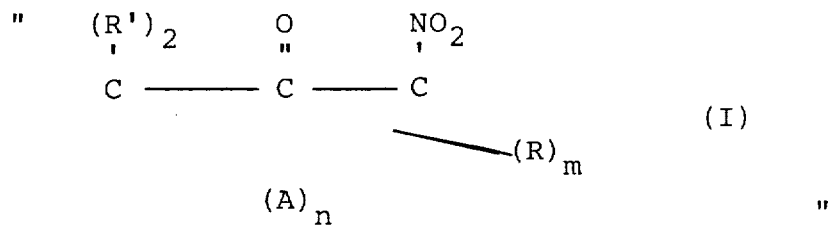

UNITED STATES PATENT AND TRADEMARK OFFICE
CERTIFICATE OF CORRECTION

PATENT NO. : 4,554,387

DATED : NOVEMBER 19, 1985

INVENTOR(S) : PAUL D. SEEMUTH

It is certified that error appears in the above-identified patent and that said Letters Patent is hereby corrected as shown below:

and should read --

(I)

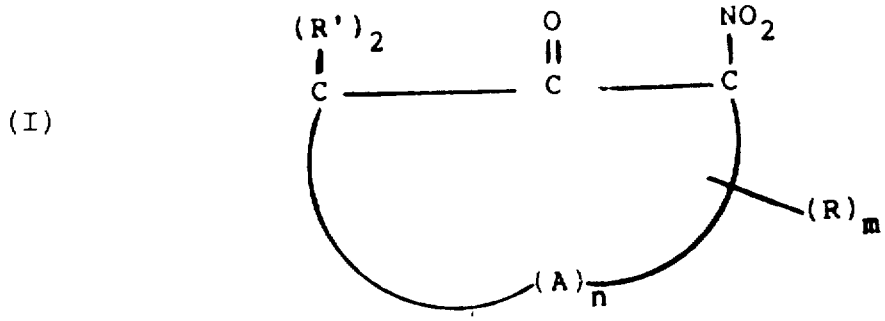

Signed and Sealed this

Eighth Day of April 1986

[SEAL]

Attest:

DONALD J. QUIGG

Attesting Officer

Commissioner of Patents and Trademarks